(12) United States Patent
Okundaye (10) Patent No.: US 10,722,681 B2
(45) Date of Patent: Jul. 28, 2020

(54) DIALYSIS CATHETER

(71) Applicant: Clifford Okundaye, Rapid City, SD (US)

(72) Inventor: Clifford Okundaye, Rapid City, SD (US)

( * ) Notice: Subject to any disclaimer, the term of this patent is extended or adjusted under 35 U.S.C. 154(b) by 489 days.

(21) Appl. No.: 15/704,272

(22) Filed: Sep. 14, 2017

(65) Prior Publication Data

US 2019/0076621 A1 Mar. 14, 2019

(51) Int. Cl.
*A61M 25/00* (2006.01)
*A61M 1/36* (2006.01)
*A61M 39/06* (2006.01)
*A61M 25/02* (2006.01)

(52) U.S. Cl.
CPC ...... *A61M 25/0032* (2013.01); *A61M 1/3653* (2013.01); *A61M 1/3661* (2014.02); *A61M 39/06* (2013.01); *A61M 25/0028* (2013.01); *A61M 2025/0031* (2013.01); *A61M 2025/0293* (2013.01)

(58) Field of Classification Search
CPC combination set(s) only.
See application file for complete search history.

(56) References Cited

U.S. PATENT DOCUMENTS

| | | | | |
|---|---|---|---|---|
| 2005/0049555 | A1* | 3/2005 | Moorehead | A61M 25/0075 604/122 |
| 2011/0301522 | A1* | 12/2011 | DeFonzo | A61M 25/0026 604/6.16 |
| 2012/0016285 | A1* | 1/2012 | Contractor | A61M 1/3653 604/6.09 |
| 2014/0155801 | A1* | 6/2014 | Zinn | A61M 39/1011 604/6.16 |

* cited by examiner

*Primary Examiner* — Kai H Weng
(74) *Attorney, Agent, or Firm* — Wick Phillips Gould & Martin LLP; Jerry C. Harris, Jr.

(57) ABSTRACT

A dialysis catheter includes an entirely subcutaneous first section, with an exterior interface via penetration of the overlying subcutaneous skin layer. In addition the first section of the dialysis catheter includes a detachable portion that enables insertion via a guidewire instead of a peel-away sheath. The dialysis catheter has a layered design that minimizes risk of infection.

7 Claims, 11 Drawing Sheets

PRIOR ART

FIG. 1

PRIOR ART

DIALYSIS CATHETER

FIELD OF THE INVENTION

The present invention is related to dialysis catheters as a means of accessing blood from the body for filtering by a dialysis machine.

BACKGROUND

Catheters have been in existence for various purposes, including draining of abscess and for urinary issues, since the 19th century. Dialysis involve the process of cleaning toxins present in large quantities in patients' blood through a filter membrane, using a pump process, and then returning the clean or dialyzed blood back to the patient. In the 1960s dialysis was discovered as a tool of improving survival in patients with end stage kidney disease or kidney failure. The patient blood is obtained from a large central vein via a dialysis catheter, which includes tubes that allow blood to be drawn from the patient, the blood then being processed through a dialysis machine and returned back to the patient through a different part of the tubes or dialysis access.

Figure 1:
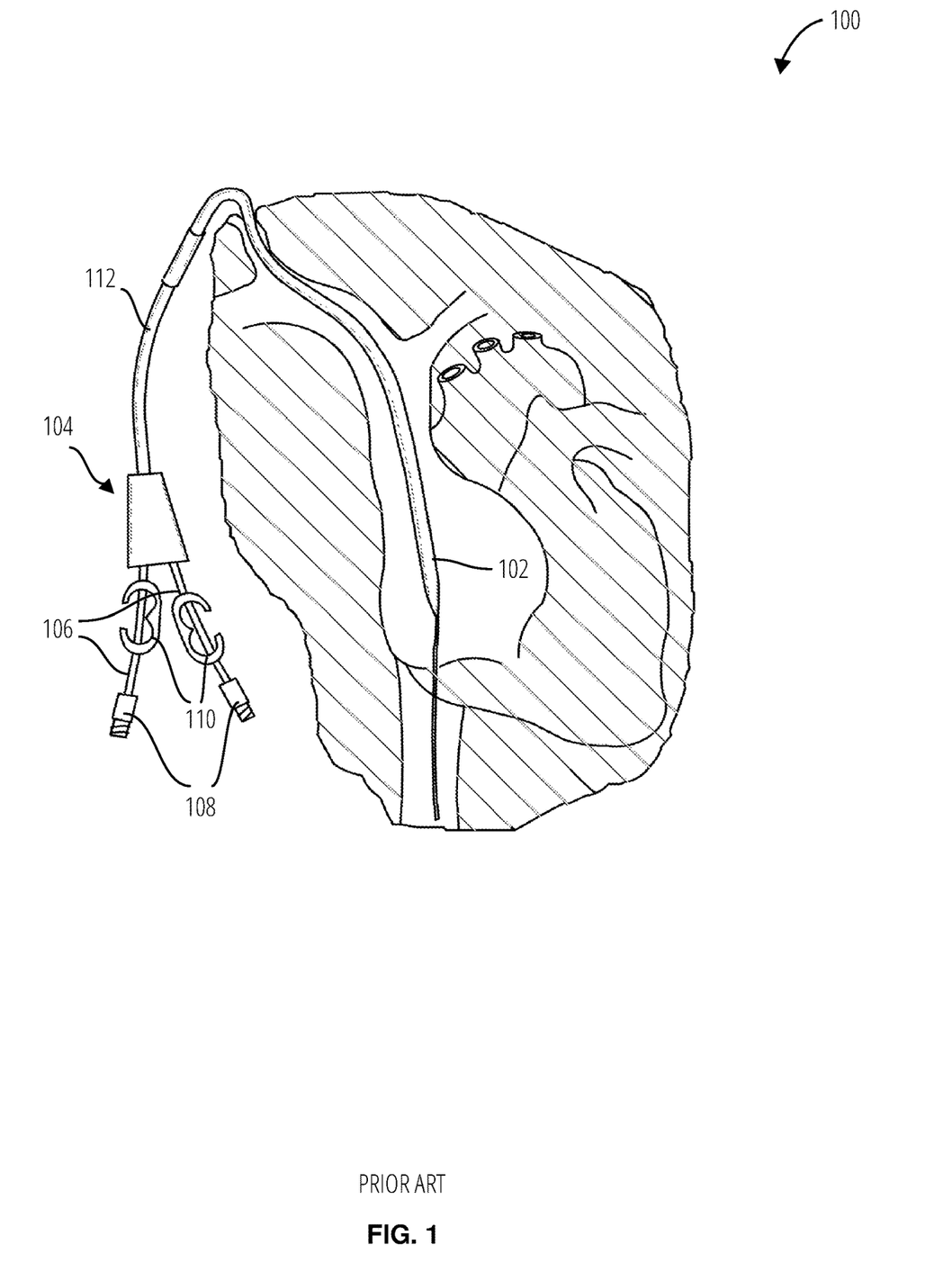
FIG. 1 illustrates a conventional in vitro dialysis catheter 100 in accordance with one embodiment.
Figure 2:
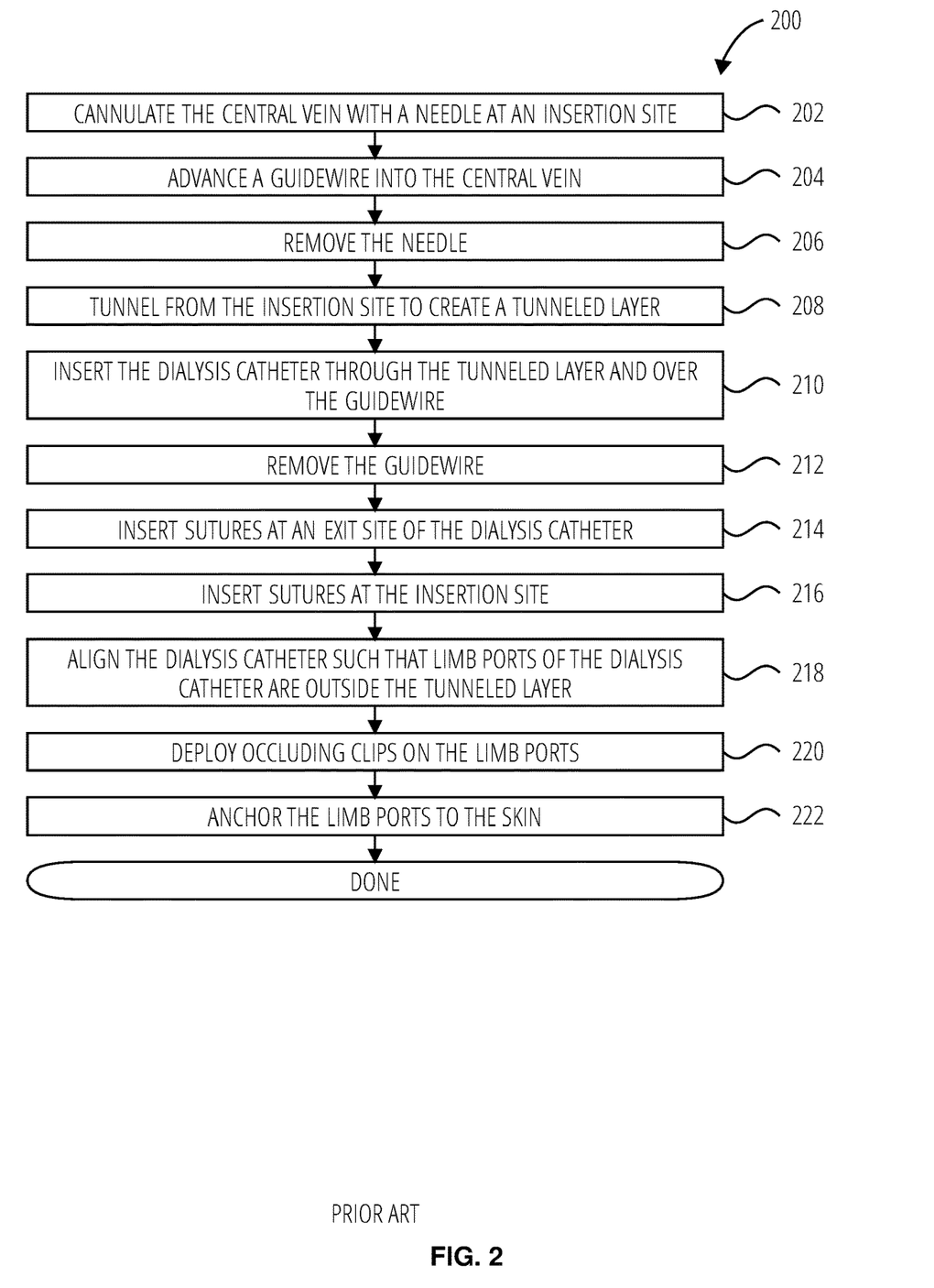
FIG. 2 illustrates a conventional dialysis catheter insertion process 200.

FIG. 1 illustrates a conventional in vitro dialysis catheter 100 in vitro, in accordance with one embodiment. The dialysis catheter 100 comprises a lumen tube 112 having a distal end 102 and a proximal end 104. The proximal end 104 bifurcates into limbs 106, each of which includes one or more clamps 110. The limbs 106 terminate at limb ports 108. FIG. 2 illustrates a dialysis catheter insertion process 200 in accordance with one embodiment. To insert the dialysis catheter, first cannulate the central vein with a needle at an insertion site 202. Next, advance a guidewire into the central vein 204, and remove the needle 206. Next, tunnel from the insertion site to create a tunneled layer 208, and insert the dialysis catheter through the tunneled layer and over the guidewire 210. Then remove the guidewire 212 and insert sutures at an exit site of the dialysis catheter 214, and insert sutures at the insertion site 216.

In some cases, a peel away sheet is deployed over the guidewire to facilitate removal of the guidewire and placement of the tunneled dialysis catheter at the insertion site. This technique may require use of a flow valve.

Next, align the dialysis catheter such that limb ports of the dialysis catheter are outside the tunneled layer 218, and deploy occluding clips on the limb ports 220, and anchor the limb ports to the skin 222.

Initially at the advent of dialysis, access to the patient blood was mainly via such tubes. Recently, AV grafts and AV fistulas have become the preferred method for accessing the blood, due to lower risk of infection. Dialysis catheters are still common in patients starting dialysis for the first time, and in many others who cannot tolerate a fistula or graft. The advantage of the dialysis catheter includes easy access and early use from the time of insertion to the time when dialysis is needed. A major disadvantage is the high risk of infection.

Studies have shown that in long term dialysis patients using a tunneled dialysis catheter, the exit site of the dialysis catheter infection is strongly correlated to the exit site bacteria contamination. Prevention of swimming or exposure to water has been tried to minimize recurrent infection or bacterial contamination of the exit site. However, the exposure of the catheter exit site to the skin results in a high chance of bacteria migrating to contaminate the dialysis catheter and subsequently cause bacteremia infections.

In the early 1990s, an entirely subcutaneous dialysis catheter called Life Site was introduced, but was not shown to decrease dialysis catheter related infections. The Life Site catheter utilized a complex valve system, involving multiple metallic and silicone layers inside the valves.

BRIEF DESCRIPTION OF THE DRAWINGS

To easily identify the discussion of any particular element or act, the most significant digit or digits in a reference number refer to the figure number in which that element is first introduced.

DETAILED DESCRIPTION

Various terms are used herein and should be accorded their conventional meaning in the relevant arts, unless otherwise defined expressly or by context.

"Cannulate herein refers to insertion of a tubular structure into a vein or body cavity.

"Exit site" herein refers to the site where the proximal portion of the catheter exits the subcutaneous surface for performing dialysis.

"Luminal flow" herein refers to the flow of blood through tubular structures of the dialysis catheter.

The high cost of treatment and the high mortality and morbidity rate of catheter related bacteremia creates an ongoing need for a dialysis catheter that is entirely subcutaneous when not in use, and that minimizes exposure to the overlying skin layer, thereby preventing exit sites from being a source of bacteremia.

A tunneled dialysis catheter is disclosed that is entirely subcutaneous after insertion and which does not utilize an opening in the skin for catheter exit when not in use, thereby minimizing risk of transmission of bacteria via the tunneled exit site from the skin surface. The tunneled dialysis catheter utilizes a minimal valve system and enables high luminal flow to minimize the need for antibiotics.

Figure 3:
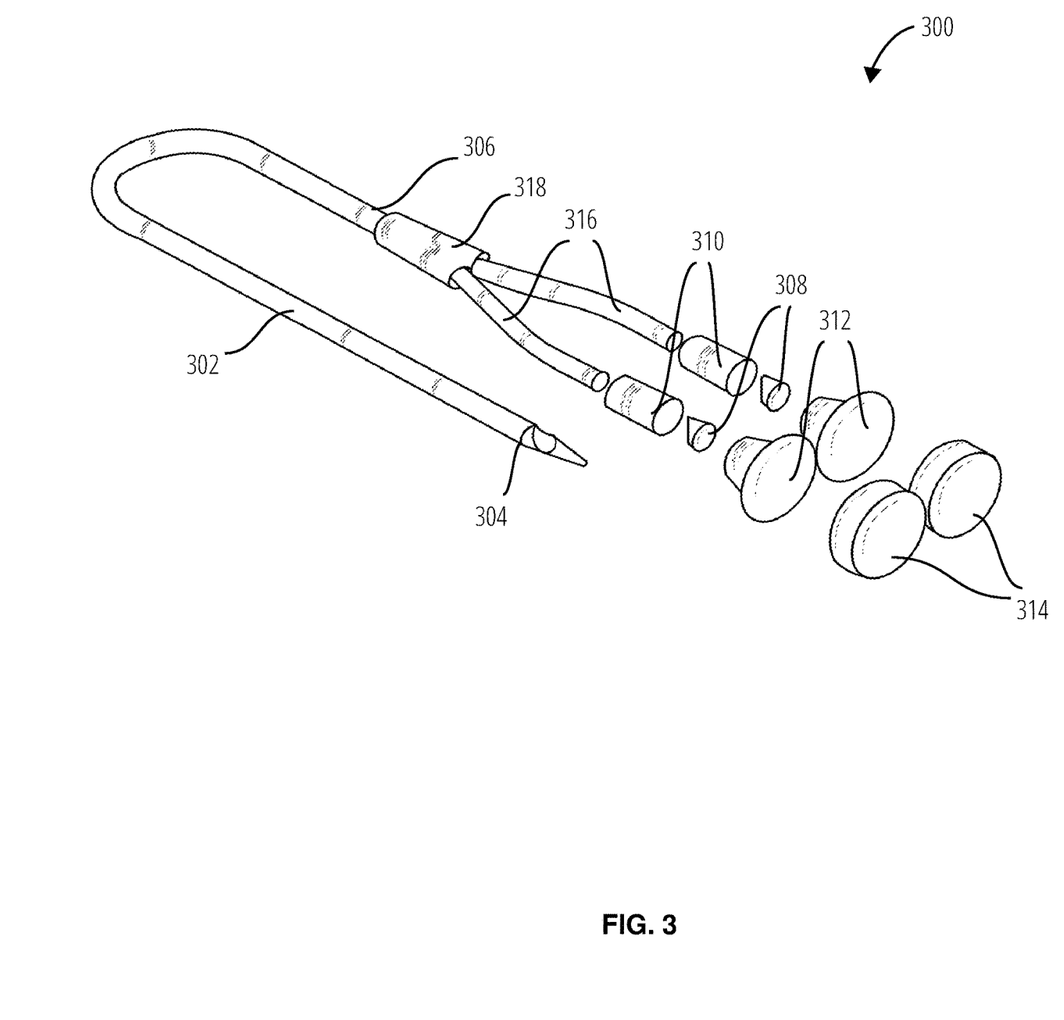
FIG. 3 illustrates a perspective view of a dialysis catheter 300 in accordance with one embodiment.
Figure 4:
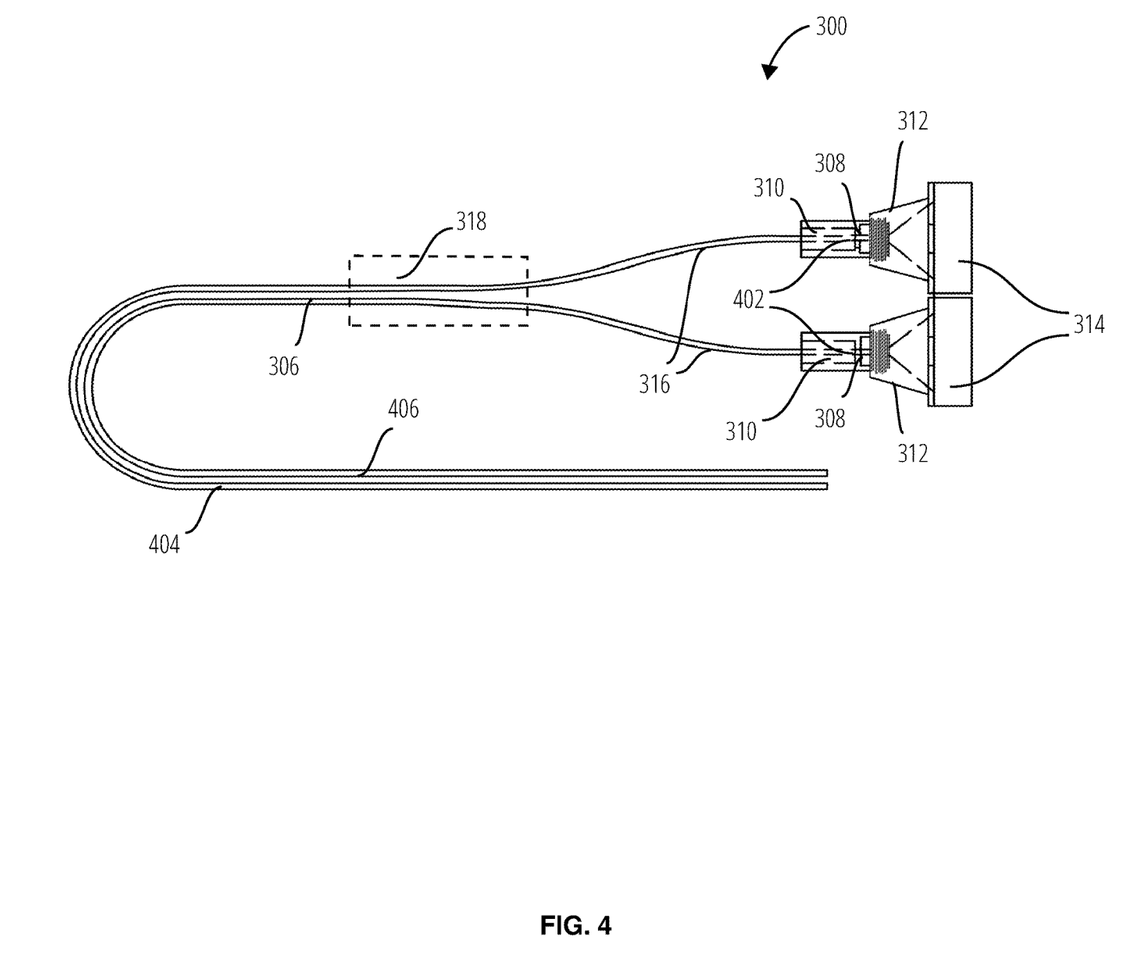
FIG. 4 illustrates a cutaway view of a dialysis catheter 300 in accordance with one embodiment.

FIG. 3 and FIG. 4 illustrate a dialysis catheter 300 in accordance with one embodiment. The dialysis catheter 300 comprises a catheter lumen tube 302 having a distal end 304 and a proximal end 306. The catheter lumen tube 302 comprises a lumen 404 for inflow and a lumen 406 for outflow. Each of the limbs 316 is terminated by a limb port 310 including a limb port 402, into which a duckbill valve 308 is disposed, followed by a needle guide 312 and cover 314. The limbs 316 at the proximal end 306 are joined into the catheter lumen tube 302 by a junction housing 318. Each of the limbs 316 is clampless.

In one embodiment, the duckbill valve 308 is retained freely (without adhesive, clips, clamps etc.) between the needle guide 312 and the limb port 310. Thus, unscrewing or otherwise detaching the needle guide 312 from the limb port 310 will free the duckbill valve 308 for removal and cleaning or replacement, for example.

Figure 5:
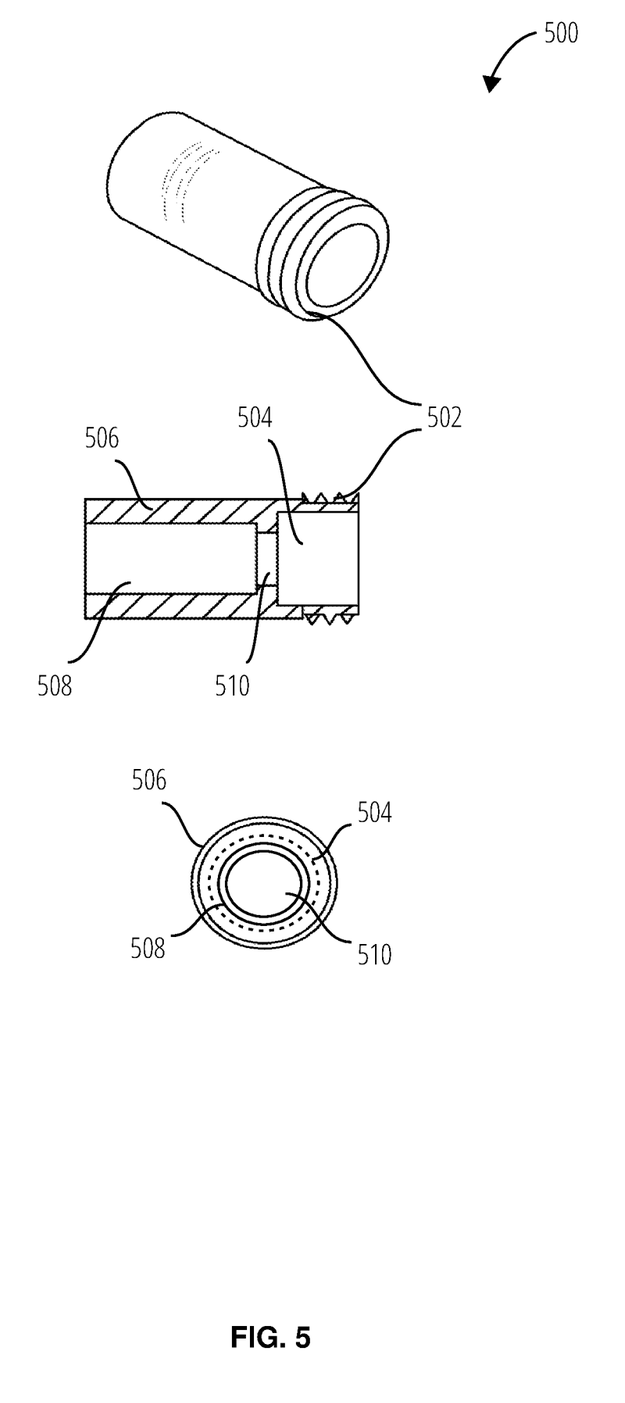
FIG. 5 illustrates a limb port 500 in accordance with one embodiment.

FIG. 5 illustrates a limb port 500 in accordance with one embodiment. The limb port 500 comprises threads 502, a valve chamber 504, a casing 506, a limb dock 508, and a transition region 510 between the limb dock 508 and the valve chamber 504.

Each of the limbs 316 is inserted and secured into the limb dock 508 of the respective limb port 310, and for each fitting a duckbill valve 308 is disposed within the valve chamber 504. In the illustrated embodiment, the needle guide 312 is secured to the limb port 500 by screwing it over the threads 502.

Figure 6:
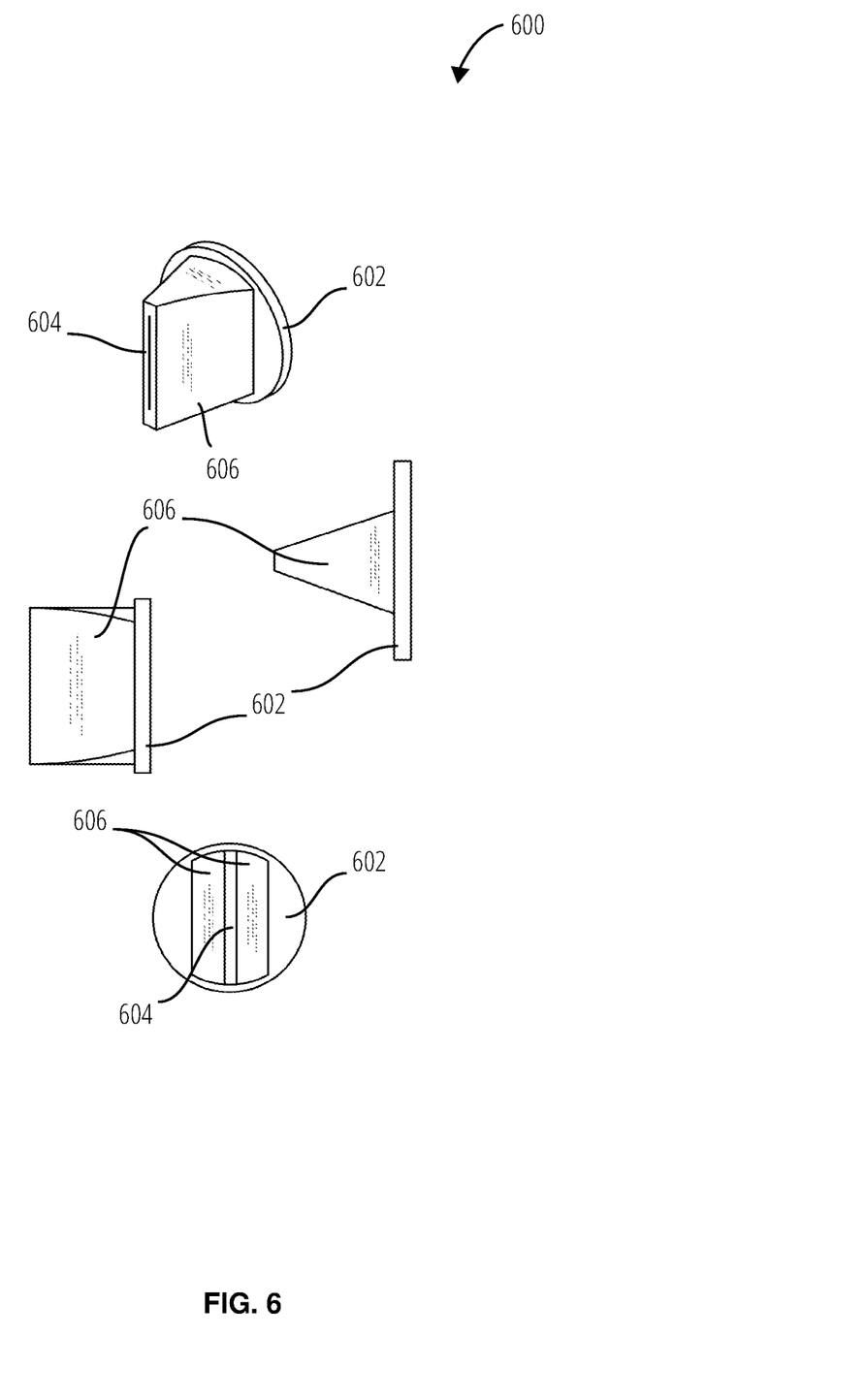
FIG. 6 illustrates a duckbill valve 600 in accordance with one embodiment.

FIG. 6 illustrates a duckbill valve 600 in accordance with one embodiment. The duckbill valve 600 comprises a stop cover 602, a valve port 604, and a port body 606.

Figure 7:
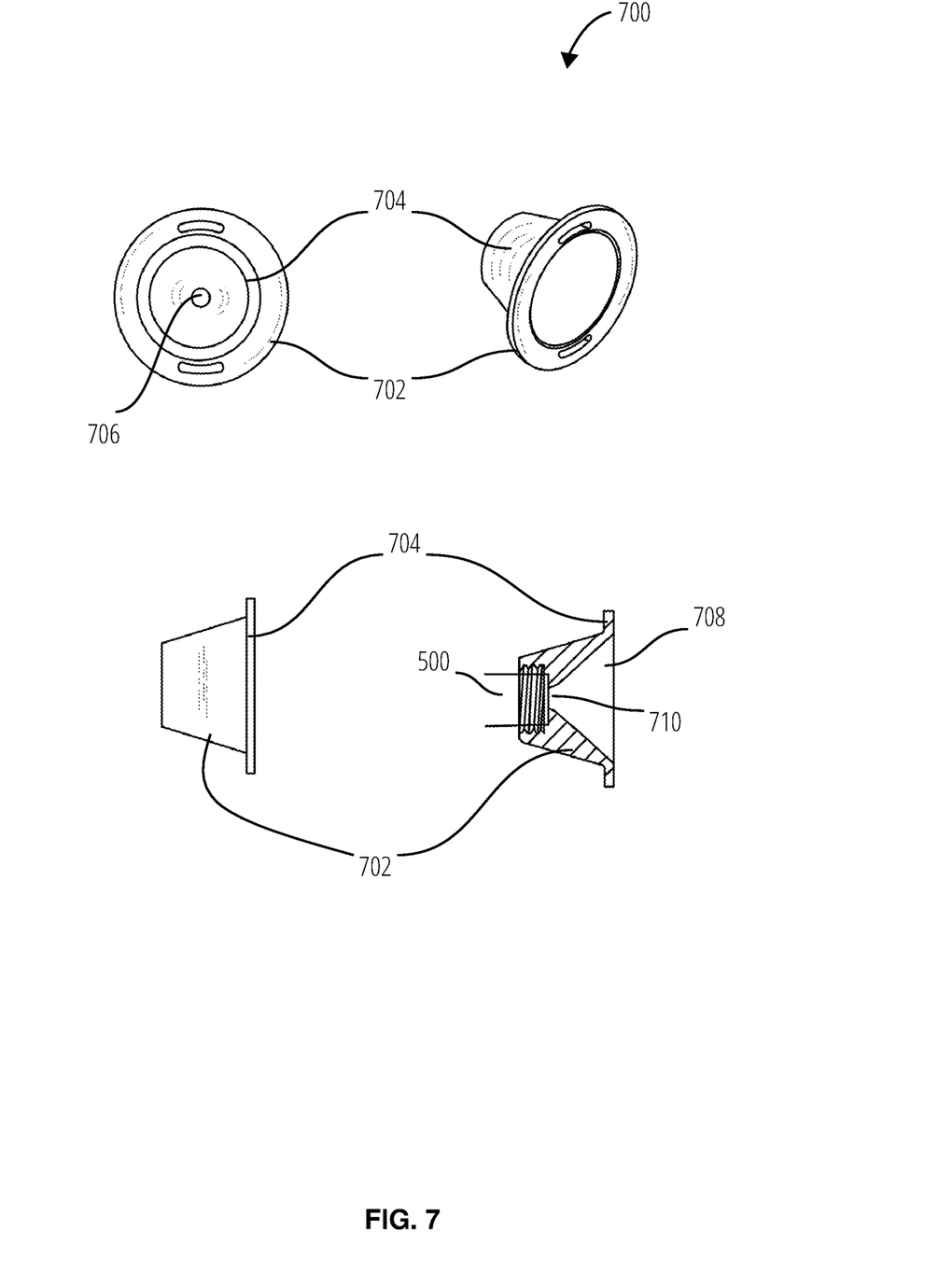
FIG. 7 illustrates a needle guide 700 in accordance with one embodiment.

FIG. 7 illustrates a needle guide 700 in accordance with one embodiment. The needle guide 700 comprises a flange 702, a tapered body 704, and a needle aperture 706. The needle guide 700 comprises internal threads to mate with the threads 502 of the limb port 500. The tapered body 704 tapers in its interior from a wide aperture 708 to a narrow aperture 710 at the interface to the duckbill valve 600.

Figure 8:
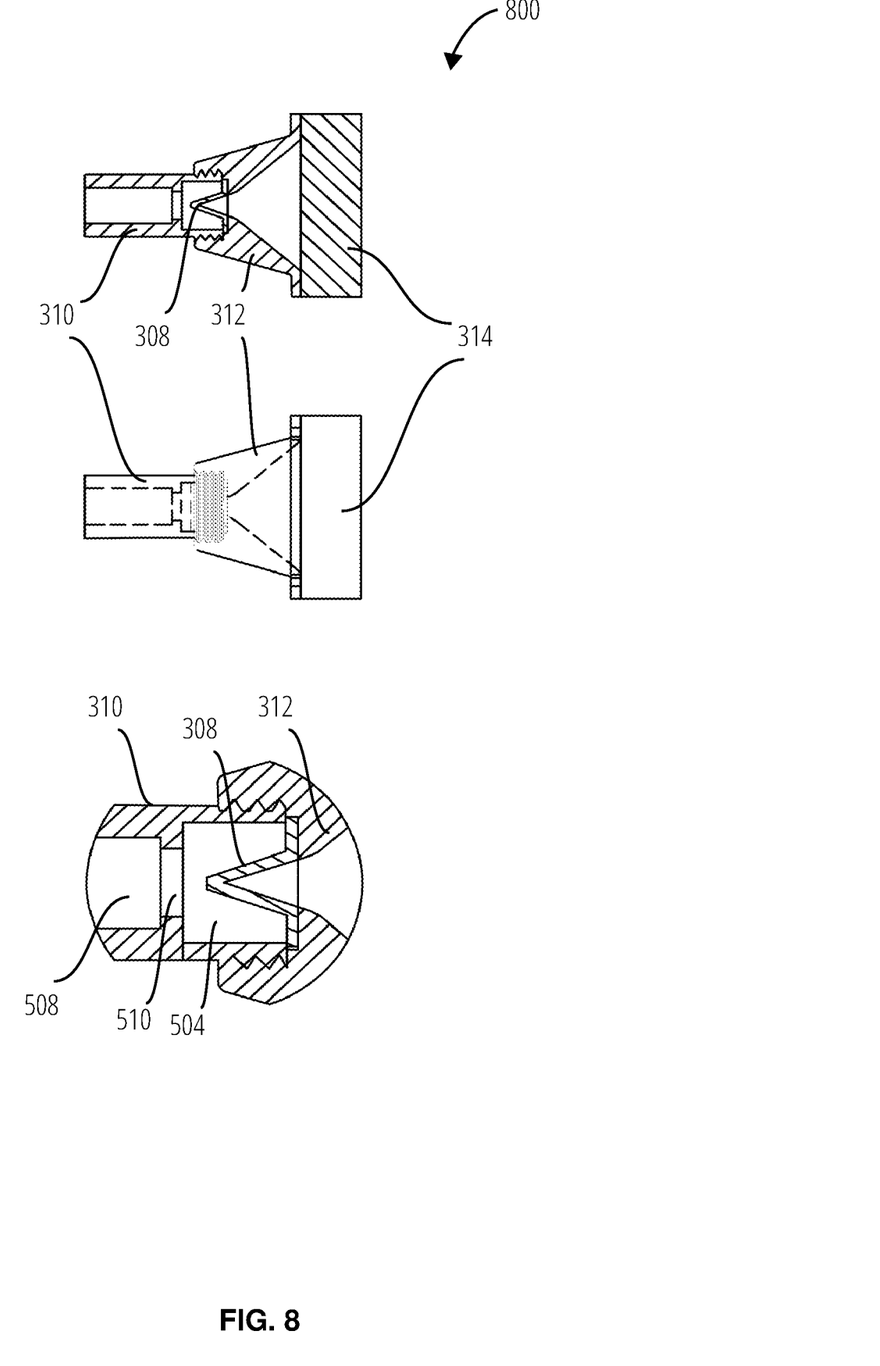
FIG. 8 illustrates a limb port assembly 800 in accordance with one embodiment.

FIG. 8 illustrates a limb port assembly 800 in accordance with one embodiment. The limb port assembly 800 is formed by inserting the duckbill valve 308 into the limb port 402 of the limb port 310, and the needle guide 312 is rotated onto the threads 502 of the limb port 310, and the cover 314 is pressure fit to the flange 702 of the needle guide 312.

Figure 9:
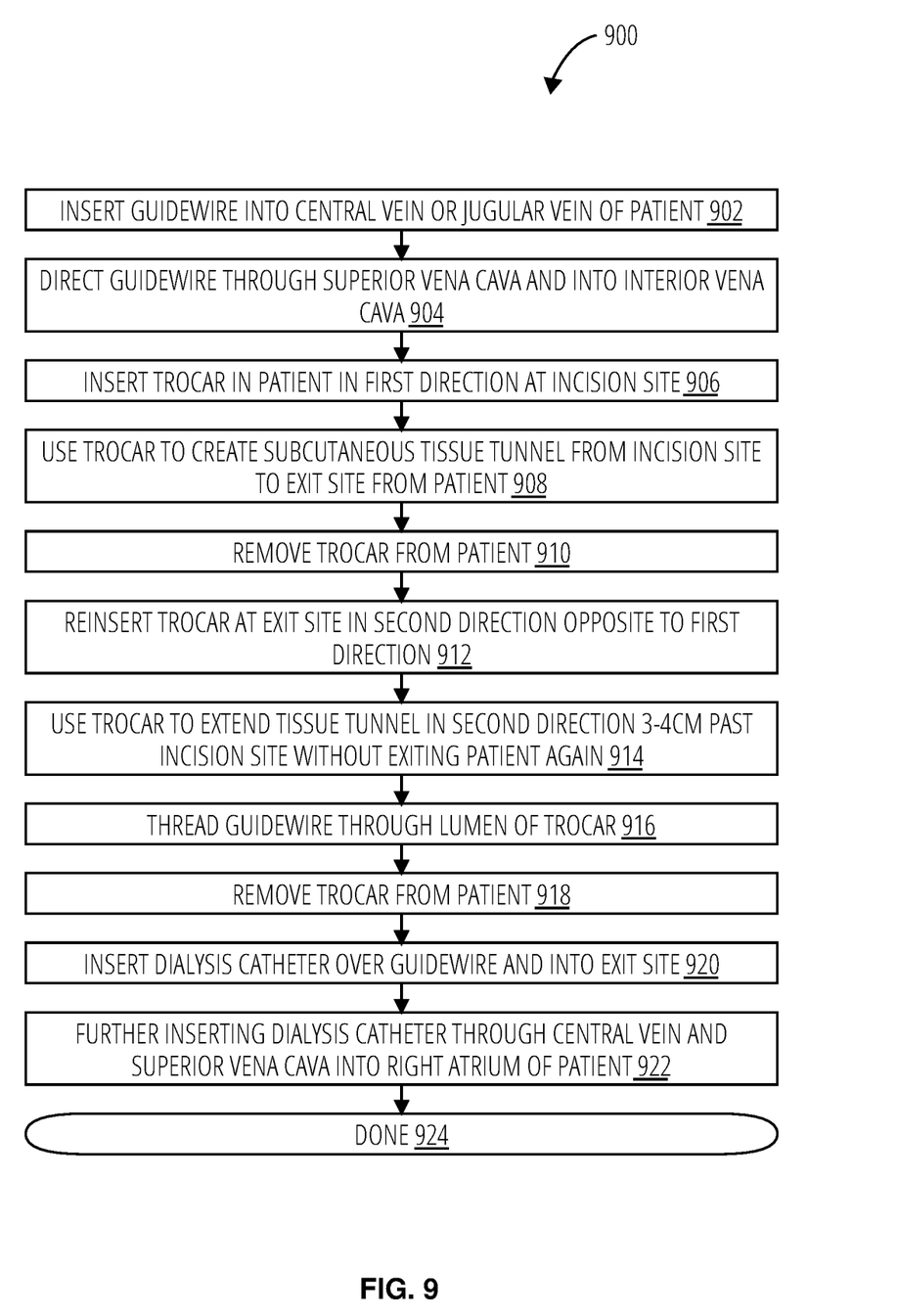
FIG. 9 illustrates a dialysis catheter insertion process 900 in accordance with one embodiment.

FIG. 9 illustrates a dialysis catheter insertion process 900 in accordance with one embodiment. In block 902 of the process 900, the medical provider inserts a guidewire into a central vein or jugular vein of the patient. In block 904, the guidewire is directed through the superior vena cava and into the interior vena cava. In block 906, a trocar is inserted into the patient in a first direction at an incision site.

In block 908, the trocar is used to create a subcutaneous tissue tunnel from the incision site to an exit site from the patient. In block 910, the trocar is removed from the patient. The subcutaneous tissue tunnel is then modified as follows.

In block 912, the trocar is inserted at the exit site in a second direction different from the first direction. In block 914, the trocar is used to extend the tissue tunnel in the second direction 3-4 cm without exiting the patient again. The patient is now prepared for insertion of the guidewire.

In block 916, the guidewire is threaded through a lumen of the trocar. In block 918, the trocar is removed from the patient, in preparation for insertion of the dialysis catheter.

In block 920, the dialysis catheter is inserted over the guidewire and into the exit site. In block 922, the dialysis catheter is further inserted through the central vein and superior vena cava into a right atrium of the patient, and the limbs are inserted into the subcutaneous tissue tunnel and the tissue tunnel extension (see FIG. 11). In done block 924, the dialysis catheter insertion process 900 ends.

Figure 10:
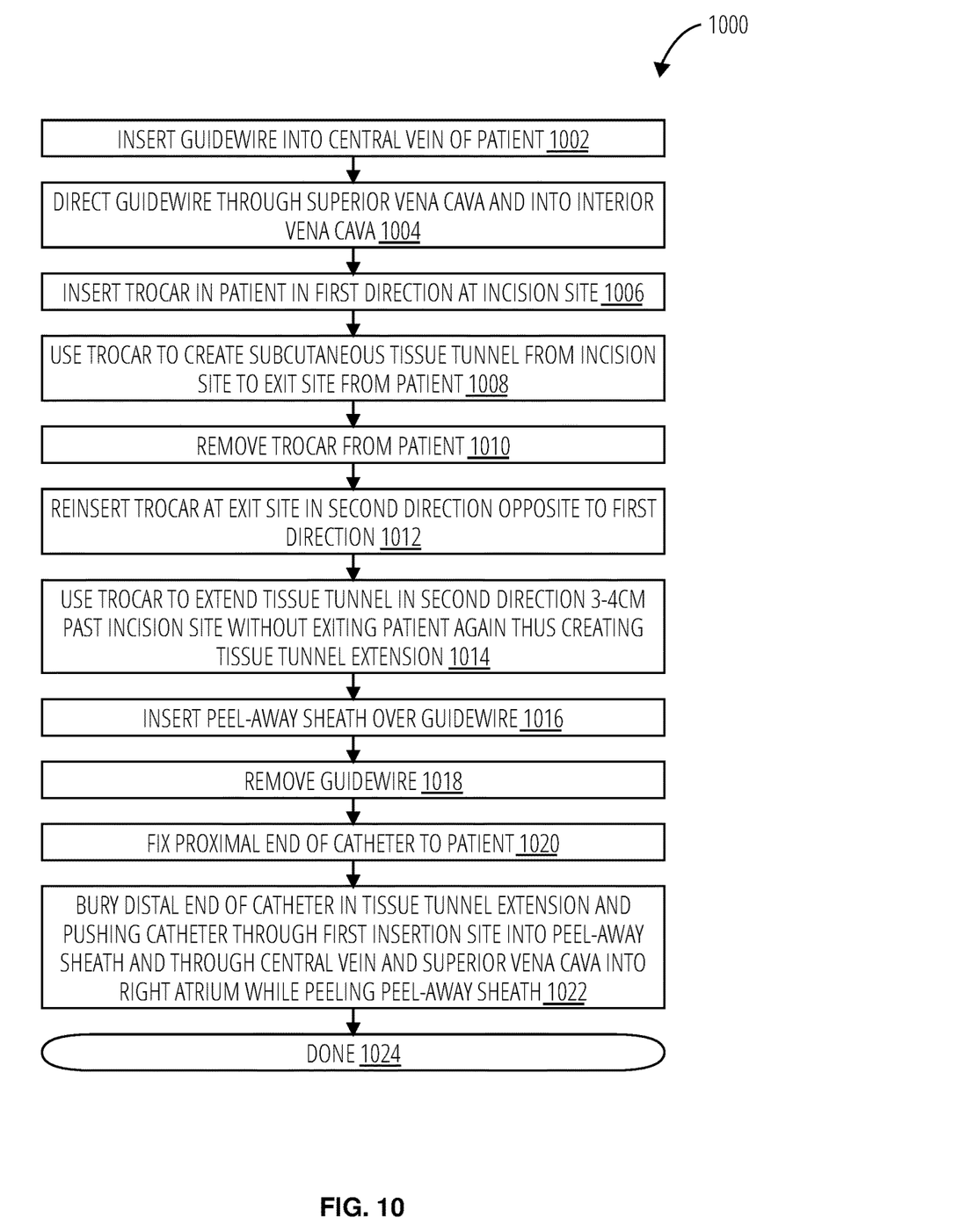
FIG. 10 illustrates a dialysis catheter insertion process 1000 in accordance with one embodiment.

FIG. 10 illustrates a dialysis catheter insertion process 1000 in accordance with another embodiment. At block 1002, the medical provider inserts a guidewire into a central vein of the patient. In block 1004, the guidewire is directed through the superior vena cava and into the interior vena cava. In block 1006, a trocar is inserted into the patient in a first direction at an incision site. In block 1008, the trocar is used to create a subcutaneous tissue tunnel from the incision site to an exit site from the patient. These blocks are similar to those described in the process 900 of FIG. 9.

In block 1010, the trocar is removed from the patient. In block 1012, the trocar is reinserted at the exit site in a second direction different from the first direction. In block 1014, the trocar is used to extend the tissue tunnel in the second direction 3-4 cm without exiting the patient again thus creating a tissue tunnel extension. At this point, the process 1000 diverges somewhat from the process 900 in FIG. 9

In block 1016, a peel-away sheath is inserted over the guidewire. In block 1018, the guidewire is removed. In block 1020, a proximal end of the catheter is fixed to the patient. In block 1022, a distal end of the catheter is buried in the tissue tunnel extension and the catheter is pushed through the first insertion site into the peel-away sheath and through the central vein and superior vena cava into the right atrium, while peeling the peel-away sheath. In done block 1024, the process 1000 ends.

Figure 11:
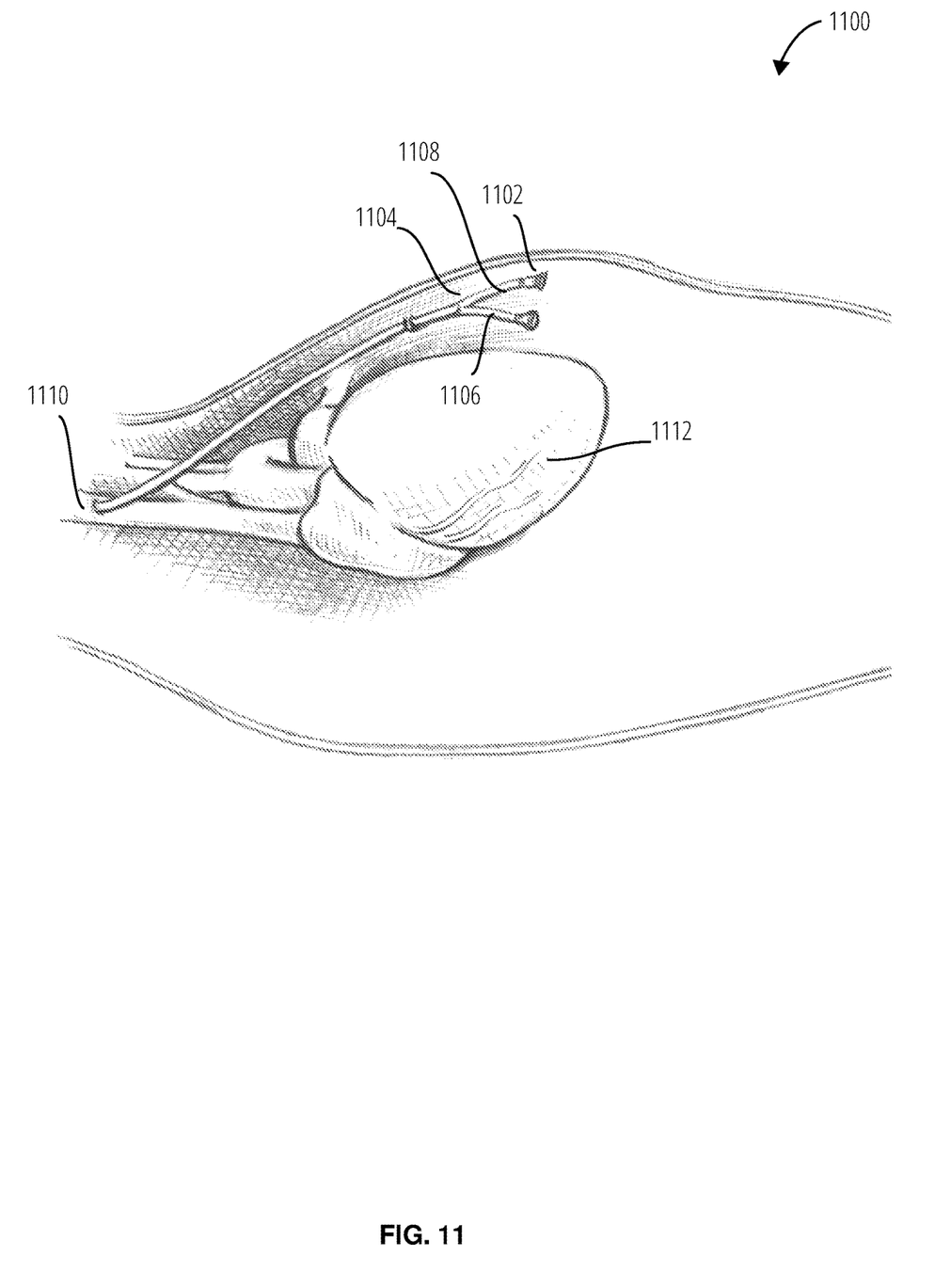
FIG. 11 illustrates an in vitro dialysis catheter 1100 in accordance with one embodiment.

FIG. 11 illustrates an in vitro dialysis catheter 1100 in accordance with one embodiment. The in vitro dialysis catheter 1100 is inserted at an incision site 1102 following, for example, a guidewire along a central vein to the superior vena cava 1110 and into the heart 1112. A trocar is utilized to form a tissue tunnel 1108 from an incision site 1102 to an exit site 1104 from which the dialysis catheter may be accessed. The trocar is also utilized to form a tissue tunnel extension 1106. When not in use, both limbs of the dialysis catheter are completely inserted (one in the tissue tunnel 1108, the other in the tissue tunnel extension 1106) in vitro and do not protrude from the body of the patient.

What is claimed is:

1. A method of inserting a dialysis catheter into a patient, the method comprising:
   inserting a trocar in the patient in a first direction at an incision site;
   using the trocar to create a subcutaneous tissue tunnel from the incision site to an exit site from the patient;
   inserting the trocar at the exit site in a second direction different from the first direction;
   using the trocar to create a tissue tunnel extension without exiting the patient again;
   inserting the dialysis catheter into the exit site;
   extending the dialysis catheter from the exit site through a central vein or jugular vein into a superior vena cava;
   configuring two limbs of the dialysis catheter each with a limb port housing a valve, a needle guide coupled to the valve, and a cover on the needle guide; and
   inserting the limbs of the dialysis catheter into the subcutaneous tissue tunnel and the tissue tunnel extension.

2. The method of claim 1, further comprising:
   extending the dialysis catheter over a guidewire from the exit site into the superior vena cava.

3. The method of claim 2, further comprising:
   deploying a peel-away sheath over the guidewire;
   removing the guidewire; and
   extending the dialysis catheter through the exit site into the peel-away sheath and into the superior vena cava while peeling the peel-away sheath.

4. The method of claim 1, the needle guide comprising an interior cavity tapered from a wide aperture to a narrow aperture at the interface to the valve.

5. The method of claim 1, wherein the valve is a duckbill valve.

6. The method of claim 5, wherein the duckbill valve is retained freely between the needle guide and the limb port.

7. The method of claim 1, wherein each limb is clampless.

* * * * *